US009044529B2

(12) United States Patent
Lu et al.

(10) Patent No.: US 9,044,529 B2
(45) Date of Patent: Jun. 2, 2015

(54) HYDROGEL TISSUE ADHESIVE FORMED FROM AMINATED POLYSACCHARIDE AND ALDEHYDE-FUNCTIONALIZED MULTI-ARM POLYETHER

(75) Inventors: Helen S. M. Lu, Wallingford, PA (US); Steven Willis Shuey, Chadds Ford, PA (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 740 days.

(21) Appl. No.: 13/129,617

(22) PCT Filed: Aug. 31, 2009

(86) PCT No.: PCT/US2009/055485
§ 371 (c)(1),
(2), (4) Date: May 17, 2011

(87) PCT Pub. No.: WO2010/059279
PCT Pub. Date: May 27, 2010

(65) Prior Publication Data
US 2011/0224724 A1 Sep. 15, 2011

Related U.S. Application Data

(60) Provisional application No. 61/115,967, filed on Nov. 19, 2008.

(51) Int. Cl.
| | |
|---|---|
| A61L 24/04 | (2006.01) |
| A61L 24/00 | (2006.01) |
| A61L 24/08 | (2006.01) |
| A61K 47/36 | (2006.01) |
| A61K 47/34 | (2006.01) |
| A61L 26/00 | (2006.01) |

(52) U.S. Cl.
CPC .............. *A61L 24/043* (2013.01); *A61K 47/36* (2013.01); *A61K 47/34* (2013.01); *A61L 26/0019* (2013.01); *A61L 26/0023* (2013.01); *A61L 24/0031* (2013.01); *A61L 24/046* (2013.01); *A61L 24/08* (2013.01)

(58) Field of Classification Search
None
See application file for complete search history.

(56) References Cited

U.S. PATENT DOCUMENTS

| | | | |
|---|---|---|---|
| 4,542,176 A | 9/1985 | Graham | |
| 4,584,188 A | 4/1986 | Graham | |
| 4,703,116 A | 10/1987 | Solarek et al. | |
| 4,731,162 A | 3/1988 | Solarek et al. | |
| 4,741,804 A | 5/1988 | Solarek et al. | |
| 4,749,800 A | 6/1988 | Jobe et al. | |
| 4,766,245 A | 8/1988 | Larkin et al. | |
| 4,839,449 A | 6/1989 | Billmers et al. | |
| 4,909,251 A | 3/1990 | Seelich | |
| 4,911,926 A | 3/1990 | Henry et al. |
| 4,929,670 A | 5/1990 | Billmers et al. |
| 5,011,918 A | 4/1991 | Bilimers et al. |
| 5,049,634 A | 9/1991 | Tsai et al. |
| 5,092,883 A | 3/1992 | Eppley et al. |
| 5,116,824 A | 5/1992 | Miyata et al. |
| 5,162,430 A | 11/1992 | Rhee et al. |
| 5,196,441 A | 3/1993 | Kunisch et al. |
| 5,217,485 A | 6/1993 | Liu et al. |
| 5,275,838 A | 1/1994 | Merrill |
| 5,283,339 A | 2/1994 | Arnold et al. |
| 5,292,802 A | 3/1994 | Rhee et al. |
| 5,308,889 A | 5/1994 | Rhee et al. |
| 5,324,775 A | 6/1994 | Rhee et al. |
| 5,328,995 A | 7/1994 | Schaulin et al. |
| 5,451,398 A | 9/1995 | Vigh |
| 5,502,042 A | 3/1996 | Gruskin et al. |
| 5,505,952 A | 4/1996 | Jiang et al. |
| 5,514,379 A | 5/1996 | Weissleder et al. |
| 5,567,685 A | 10/1996 | Linden et al. |
| 5,643,575 A | 7/1997 | Martinez et al. |
| 5,733,563 A | 3/1998 | Fortier |
| 5,776,706 A | 7/1998 | Siiman et al. |

(Continued)

FOREIGN PATENT DOCUMENTS

| | | |
|---|---|---|
| EP | 0961783 | 1/2007 |
| JP | 1982-102932 | 6/1982 |

(Continued)

OTHER PUBLICATIONS

Rebizak, R., Schaefer, M., & Dellacherie, É. (1999). Macromolecular contrast agents for magnetic resonance imaging: influence of polymer content in ligand on the paramagnetic properties. European journal of pharmaceutical sciences, 7(3), 243-248.*
Thome, J., et al., "Ultrathin Antibacterial Polyammonium Coatings on Polymer Surfaces"; Surface and Coatings Technology, 174-175, 2003, pp. 584-587.
Harris, J. Milton, "Laboratory Synthesis of Polyethylene Glycol Derivatives", JMS—Rev., Macromol. Chem. Phys., C25(3), 1985, pp. 325-373.
Harris, J. Milton, et al., "Synthesis of New Poly(Ethylene Glycol) Derivatives", PolyEthylene Glycol Chemistry: Biotechnical and Biomedical Applications, edited by Milton J. Harris, Plenum Press: New York, 1992, pp. 371-381.

(Continued)

*Primary Examiner* — Shaojia Anna Jiang
*Assistant Examiner* — Dale R Miller
(74) *Attorney, Agent, or Firm* — McCarter & English

(57) ABSTRACT

A hydrogel tissue adhesive formed by reacting an aminated polysaccharide with a water-dispersible, aldehyde-functionalized multi-arm polyether is described. The hydrogel tissue adhesive may be useful as a general tissue adhesive and sealant for medical and veterinary applications such as wound closure, supplementing or replacing sutures or staples in internal surgical procedures such as intestinal anastomosis and vascular anastomosis, tissue repair, ophthalmic procedures, drug delivery, and to prevent post-surgical adhesions. Additionally, due to the presence of the aminated polysaccharide, the hydrogel tissue adhesive may also promote wound healing and blood coagulation, and provide antimicrobial properties.

16 Claims, No Drawings

(56) References Cited

U.S. PATENT DOCUMENTS

| | | | |
|---|---|---|---|
| 5,830,986 A | 11/1998 | Merrill et al. | |
| 5,840,698 A | 11/1998 | Campbell et al. | |
| 5,843,865 A | 12/1998 | Del Corral et al. | |
| 5,874,500 A | 2/1999 | Rhee et al. | |
| 5,990,237 A | 11/1999 | Bentley et al. | |
| 6,051,648 A | 4/2000 | Rhee et al. | |
| 6,121,375 A | 9/2000 | Eknoian | |
| 6,150,472 A | 11/2000 | Engbers | |
| 6,165,488 A | 12/2000 | Tardy et al. | |
| 6,166,130 A | 12/2000 | Rhee et al. | |
| 6,323,278 B2 | 11/2001 | Rhee et al. | |
| 6,391,939 B2 | 5/2002 | Tayot et al. | |
| 6,410,519 B1 | 6/2002 | Gruskin et al. | |
| 6,458,147 B1 | 10/2002 | Cruise et al. | |
| 6,458,889 B1 | 10/2002 | Trollsas et al. | |
| 6,465,694 B1 | 10/2002 | Baudys et al. | |
| 6,514,534 B1 | 2/2003 | Sawhney | |
| 6,534,591 B2 | 3/2003 | Rhee et al. | |
| 6,602,952 B1 | 8/2003 | Bentley et al. | |
| 6,620,125 B1 | 9/2003 | Redl | |
| 6,689,399 B1 | 2/2004 | Dickson | |
| 6,696,089 B2 | 2/2004 | Kabanov et al. | |
| 6,703,047 B2 | 3/2004 | Sawhney et al. | |
| 6,756,518 B2 | 6/2004 | Gruskin et al. | |
| 6,800,278 B1 | 10/2004 | Perrault et al. | |
| 6,833,408 B2 | 12/2004 | Sehl et al. | |
| 6,858,736 B2 | 2/2005 | Nho et al. | |
| 6,896,725 B2 | 5/2005 | Thornton et al. | |
| 6,958,325 B2 | 10/2005 | Domb | |
| 7,001,891 B1 | 2/2006 | Domb | |
| 7,196,180 B2 | 3/2007 | Aeschlimann et al. | |
| 7,217,845 B2 | 5/2007 | Rosen et al. | |
| 7,255,999 B2 | 8/2007 | Singh et al. | |
| 7,459,185 B2 | 12/2008 | Gutowski et al. | |
| 7,780,980 B2 | 8/2010 | Sawhney | |
| 7,834,065 B2 | 11/2010 | Nakajima et al. | |
| 7,854,923 B2 | 12/2010 | Chen et al. | |
| 7,868,132 B2 | 1/2011 | Chenault | |
| 7,883,694 B2 | 2/2011 | Rhee et al. | |
| 8,202,963 B2 | 6/2012 | Chenault et al. | |
| 8,241,609 B2 | 8/2012 | Figuly et al. | |
| 8,466,327 B2 | 6/2013 | Arthur | |
| 8,545,871 B2 | 10/2013 | Arthur et al. | |
| 8,551,136 B2 | 10/2013 | Lu | |
| 8,580,950 B2 | 11/2013 | Lu et al. | |
| 8,580,951 B2 | 11/2013 | Lu et al. | |
| 2002/0151520 A1 | 10/2002 | Gruskin | |
| 2003/0022216 A1 | 1/2003 | Mao | |
| 2003/0027788 A1 | 2/2003 | Singh et al. | |
| 2003/0064502 A1 | 4/2003 | Illman et al. | |
| 2003/0087111 A1 | 5/2003 | Hubbell et al. | |
| 2003/0108511 A1 | 6/2003 | Sawhney | |
| 2003/0119985 A1 | 6/2003 | Sehl et al. | |
| 2004/0086479 A1 | 5/2004 | Grinstaff et al. | |
| 2004/0096507 A1 | 5/2004 | Kwang et al. | |
| 2004/0225097 A1 | 11/2004 | Nho et al. | |
| 2004/0235708 A1 | 11/2004 | Rhee et al. | |
| 2005/0002893 A1 | 1/2005 | Goldmann | |
| 2005/0020805 A1 | 1/2005 | Sunkara et al. | |
| 2005/0288684 A1 | 12/2005 | Aronson et al. | |
| 2006/0078536 A1 | 4/2006 | Kodokian et al. | |
| 2006/0110427 A1 | 5/2006 | Molock et al. | |
| 2006/0115531 A1 | 6/2006 | Chenault | |
| 2006/0292030 A1 | 12/2006 | Odermatt et al. | |
| 2007/0031467 A1 | 2/2007 | Abrahams et al. | |
| 2007/0048251 A1 | 3/2007 | Arthur | |
| 2007/0249870 A1 | 10/2007 | Chenault | |
| 2008/0004421 A1 | 1/2008 | Chenault et al. | |
| 2008/0031824 A1* | 2/2008 | Smyth et al. | 424/40 |
| 2008/0051323 A1 | 2/2008 | Kosak | |
| 2008/0220047 A1 | 9/2008 | Sawhney et al. | |
| 2008/0319101 A1 | 12/2008 | Nakajima et al. | |
| 2009/0035249 A1 | 2/2009 | Bhatia et al. | |
| 2009/0054535 A1 | 2/2009 | Figuly et al. | |
| 2010/0015231 A1 | 1/2010 | Lu | |
| 2010/0086678 A1 | 4/2010 | Arthur et al. | |
| 2010/0112063 A1 | 5/2010 | Figuly et al. | |
| 2010/0160960 A1 | 6/2010 | Wagman et al. | |
| 2010/0255101 A1 | 10/2010 | Lu | |
| 2010/0272804 A1 | 10/2010 | Lu | |
| 2011/0224724 A1 | 9/2011 | Lu et al. | |
| 2012/0035129 A1 | 2/2012 | Wagman | |
| 2012/0094955 A1 | 4/2012 | Wagman | |
| 2012/0148523 A1 | 6/2012 | Lu et al. | |

FOREIGN PATENT DOCUMENTS

| | | | |
|---|---|---|---|
| JP | 1988-11167 | 1/1988 | |
| WO | WO 87/00836 | 2/1987 | |
| WO | WO 90/10441 | 9/1990 | |
| WO | WO 91/15368 | 10/1991 | |
| WO | WO 97/30103 | 8/1997 | |
| WO | WO 99/01143 | 1/1999 | |
| WO | WO 00/69925 | 11/2000 | |
| WO | WO 01/49268 | 7/2001 | |
| WO | WO 01/72280 | 10/2001 | |
| WO | WO 01/87986 | 11/2001 | |
| WO | WO 02/102864 | 12/2002 | |
| WO | WO 03/020818 | 3/2003 | |
| WO | WO 03/097759 | 11/2003 | |
| WO | WO 2006/031358 | 3/2006 | |
| WO | WO 2006/042161 | 4/2006 | |
| WO | WO 2006/080523 | 8/2006 | |
| WO | WO 2006/086510 | 8/2006 | |
| WO | WO 2008/005207 | 1/2008 | |
| WO | WO 2008/066787 | 6/2008 | |
| WO | WO 2008066787 A2 * | 6/2008 | ............ C08G 65/00 |
| WO | WO 2009/064977 | 5/2009 | |
| WO | WO 2010/059279 | 5/2010 | |
| WO | WO 2010/059280 | 5/2010 | |
| WO | WO 2010/111570 | 9/2010 | |
| WO | WO 2010/118284 | 10/2010 | |

OTHER PUBLICATIONS

Chen, Nicole, et al., "Mechanisms of Aldehyde-Containing Paper Wet-Strength Resins", Industrial & Engineering Chemistry Research, vol. 41, No. 22, 2002, pp. 5366-5371.

Callant, Dominique, et al., "A New Approach to Dextran Derivatives with Pendent Aldehyde Groups", Reactive Polymers, vol. 8, 1988, pp. 129-136.

Hollander, Andreas, et al., "Polymer Surface Chemistry for Biologically Active Materials", Applied Surface Science, vol. 235, 2004, pp. 145-150.

Stone, H. Harlan, et al., "Antibiotic Prophylaxis in Gastric, Biliary and Colonic Surgery", Ann. Surg; Oct. 1976, pp. 443-450.

Fishman, Alexander, et al., "Synthesis and Investigation of Novel Branched PEG-Based Soluble Polymer Supports", The Journal of Organic Chemistry, vol. 68, 2003, pp. 9843-9846.

Newkome, George R., "Improved Synthesis of an Ethereal Tetraamine Core for Dendrimer Construction", The Journal of Organic Chemistry, vol. 67, 2002, pp. 3957-3960.

Halabi, A., et al., "Synthesis and Characterization of a Novel Dendritic Acrylic Monomer", The Journal of Organic Chemistry, vol. 65, 2000, pp. 9210-9213.

Harris, J. Milton, et al., "Synthesis and Characterization of Poly(ethylene Glycol) Derivatives", Journal of Polymer Science: Polymer Chemistry Edition, vol. 22, 1984, pp. 341-352.

Merrill, Edward W., "Poly(ethylene oxide) Star Molecules: Synthesis, Characterization, and Applications in Medicine and Biology", Journal of Biomaterials Science Polymer Edition, vol. 5, No. 1/2, 1993, pp. 1-11.

Zhao, Xuan, et al., "Novel Degradable Poly(ethylene glycol) Esters for Drug Delivery", Poly(ethylene glycol) Chemistry and Biological Applications, Oxford University Press, 1998, Chapter 28, pp. 458-472.

Azzam, Tony, et al., "Cationic Polysaccharides for Gene Delivery", Macromolecules, vol. 35, No. 27, 2002, pp. 9947-9953.

Nagasaki, Yukio, et al., "Formyl-Ended Heterobifunctional Poly(ethylene oxide): Synthesis of Poly(ethylene oxide) with a Formyl Group at One End and a Hydroxyl Group at the Other End", Bioconjugate Chemistry, vol. 6, No. 2, 1995, pp. 231-233.

(56) References Cited

OTHER PUBLICATIONS

Greenwald, Richard B., et al., "Drug Delivery Systems Employing 1,4- or 1,6-Elimination: Poly(ethylene glycol) Prodrugs of Amine-Containing Compounds", Journal of Medicinal Chemistry, vol. 42, No. 18, 1999, pp. 3657-3667.

Zalipsky, Samuel, et al., "Preparation and Applications of Polyethylene Glycol—Polystyrene Graft Resin Supports for Solid-Phase Peptide Synthesis", Reactive Polymers, vol. 22, 1994, pp. 243-258.

Lara, V.S., et al., "Dentin-Induced In Vivo Inflammatory Response and In Vitro Activation of Murine Macrophages", Journal of Dental Research, vol. 82, No. 6, 2003, pp. 460-465.

Atassi, M.Z., "Immunochemistry of Proteins", vol. 1, Plenum Press, New York, 1977, pp. 59-60.

Sweeney, Thomas, et al., "Intestinal Anastomoses Detected with a Photopolymerized Hydrogel", Surgery, vol. 131, No. 2, Feb. 2002, pp. 185-189.

Kim, Jae Chan, et al., "Evaluation of Tissue Adhesives in Closure of Scleral Tunnel Incisions", Journal of Cataract & Refractive Surgery, vol. 21, May 1995, pp. 320-325.

Sarayba, Melvin A., et al., "Inflow of Ocular Surface Fluid Through Clear Corneal Cataract Incisions: A Laboratory Model", American Journal of Ophthalmology, vol. 138, No. 2, Aug. 2004, pp. 206-210.

Buckmann, Andreas F., et al., "Functionalization of Poly(ethylene glycol) and Monomethoxy-Poly(ethylene glycol)", Makromolecular Chemistry, vol. 182, 1981, pp. 1379-1384.

Bruce, J., et al., "Systematic Review of the Definition and Measurement of Anastomotic Leak after Gastrointestinal Surgery", British Journal of Surgery, vol. 88, 2001, pp. 1157-1168.

Mo, Xiumei, et al,, "Soft Tissue Adhesive Composed of Modified Gelatin and Polysaccharides", Journal of Biomaterials Science Polymer Edition, vol. 11, No. 4, 2000, pp. 341-351.

Hofreiter, B.T., et al., "Rapid Estimation of Dialdehyde Content of Periodate Oxystarch through Quantitative Alkali Consumption", Analytical Chemistry, vol. 27, No. 12, Dec. 1955, pp. 1930-1931.

Zhao, Huiru, et al., "Determination of Degree of Substitution of Formyl Groups in Polyaldehyde Dextran by the Hydroxylamine Hydrochloride Method", Pharmaceutical Research, vol. 8, No. 3, 1991, pp. 400-402.

Kurisawa, Motoichi, et al., "Double-Stimuli-Responsive Degradation of Hydrogels Consisting of Oligopeptide-Terminated Poly(ethylene glycol) and Dextran with an Interpenetrating Polymer Network", Journal of Biomaterials Science Polymer Edition, vol. 8, No. 9, 1997, pp. 691-708.

Pfannemuller, B., et al., "Chemical Modification of the Surface of the Starch Granules", Starch/Starke, vol. 95, No. 9, 1983, pp. 298-303.

Specification of U.S. Appl. No. 13/102,262.

BASF Corp, Technical Bulletin, Pluronic F108 Block Copolymer Surfactant, (2004), 1 Page.

Ahmad, Shavej, et al., "Dextran and 5-aminosalicylic Acid (5-ASA) Conjugates: Synthesis, Characterisation and Enzymic Hydrolysis", Carbohydrate Research, vol. 341, 2006, pp. 2694-2701.

Cortesi, Rita, et al., "Dextran Cross-Linked Gelatin Microspheres as a Drug Delivery System", European Journal of Pharmaceutics and Biopharmaceutics, vol. 47, 1999, pp. 153-160.

Gill, Inderbir S., et al., "Improved Hemostasis During Laparoscopic Partial Nephrectomy Using Gelatin Matrix Thrombin Sealant", Adult Urology, vol. 64, No. 3, 2005, pp. 463-466.

Yao, Zhong, et al., "A Series of Novel Chitosan Derivatives: Synthesis, Characterization and Micellar Solubilization of Paclitaxel", Carbohydrate Polymers, 2007, vol. 68, pp. 781-792.

Balakrishnan, Biji, et al., "Self-cross-linking biopolymers as injectable in situ forming biodegradable scaffolds", Biomaterials, 2005, vol. 26, pp. 3941-3951.

Rebizak, Richard, et al., "Macromolecular contrast agents for magnetic resonance imaging influence of polymer content in ligand on the paramagnetic properties", European Journal of Pharmaceutical Sciences, 1999, vol. 7, pp. 243-248.

Zalipsky, Samuel, et al., "Hydrazide Derivatives of Poly(ethylene glycol) and Their Bioconjugates", ACS Symposium Series; American Chemical Society, 1997, pp. 318-341.

Sgouras, D., et al., "Method for the evaluation of biocompatibility of soluble synthetic polymers which have potential for biomedical use: 1—Use of the tetrazolium-based colorimetric assay (MTT) as a preliminary screen for evaluation of in vitro cytotoxicity", Journal of Materials Sciences: Materials in Medicine, 1990, vol. 1, pp. 61-68.

* cited by examiner

HYDROGEL TISSUE ADHESIVE FORMED FROM AMINATED POLYSACCHARIDE AND ALDEHYDE-FUNCTIONALIZED MULTI-ARM POLYETHER

CROSS-REFERENCE TO RELATED APPLICATIONS

This application is a national stage application filed under 35 USC Section 371 of PCT/US2009/055485, filed Aug. 31, 2009, which claims the benefit of U.S. Provisional Application Ser. No. 61/115,967, filed Nov. 19, 2008, both of which are incorporated herein, in entirety, by reference.

FIELD OF THE INVENTION

The invention relates to the field of medical adhesives and sealants. More specifically, the invention relates to a hydrogel tissue adhesive formed by reacting an aminated polysaccharide containing primary amine groups with a water-dispersible, aldehyde-functionalized multi-arm polyether.

BACKGROUND OF THE INVENTION

Tissue adhesives have many potential medical applications, including wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, the fibrin-based adhesives do not bond covalently to the underlying tissue.

Several types of hydrogel tissue adhesives have been developed, which have improved adhesive and cohesive properties and are nontoxic. These hydrogels are generally formed by reacting a component having nucleophilic groups with a component having electrophilic groups, which are capable of reacting with the nucleophilic groups of the first component, to form a crosslinked network via covalent bonding. However, these hydrogels typically swell or dissolve away too quickly, or lack sufficient adhesion or mechanical strength, thereby decreasing their effectiveness as surgical adhesives.

Kodokian et al. (copending and commonly owned U.S. Patent Application Publication No. 2006/0078536) describe hydrogel tissue adhesives formed by reacting an oxidized polysaccharide with a water-dispersible, multi-arm polyether amine. These adhesives provide improved adhesion and cohesion properties, crosslink readily at body temperature, maintain dimensional stability initially, do not degrade rapidly, and are nontoxic to cells and non-inflammatory to tissue. However, a tissue adhesive having these properties and also comprising a cationic polysaccharide to promote wound healing and blood coagulation, and provide antimicrobial properties would be highly desirable. Additionally, oxidized polysaccharides are known to have limited long-term stability when stored in aqueous solutions, which may restrict their commercial use.

Bentley et al. (U.S. Pat. No. 6,602,952) describe hydrogels derived from chitosan and poly(ethylene glycol), which are said to be useful as a drug delivery device, surgical sealant, or as a delivery system for a medical imaging agent. However, hydrogels derived from chitosan typically have poor mechanical properties because the poor aqueous solubility of chitosan limits the solids content that can be attained. Therefore, the need exists for a tissue adhesive that has good adhesion and mechanical strength, comprises a cationic polysaccharide to promote wound healing and blood coagulation, provides antimicrobial properties, and is formed from components that are stable in aqueous solution.

SUMMARY OF THE INVENTION

A hydrogel tissue adhesive formed by reacting an aminated polysaccharide containing primary amine groups with a water-dispersible, aldehyde-functionalized multi-arm polyether is provided.

In one embodiment a kit is provided, the kit comprising:
a) at least one aminated polysaccharide containing primary amine groups, said at least one aminated polysaccharide having a weight-average molecular weight of about 1,000 to about 1,000,000 Daltons and an equivalent weight per primary amine group of about 100 to about 3400 Daltons, wherein the at least one aminated polysaccharide is not chitosan; and
b) at least one water-dispersible, aldehyde-functionalized multi-arm polyether having at least three arms wherein at least three of the arms are terminated with an aldehyde group, wherein said water-dispersible, aldehyde-functionalized multi-arm polyether has a number-average molecular weight of about 450 to about 200,000 Daltons.

In another embodiment a dried hydrogel product formed by a process comprising the following steps is provided:
a) combining (i) a first solution or dispersion comprising at least one aminated polysaccharide containing primary amine groups in a first solvent, said aminated polysaccharide having a weight-average molecular weight of about 1,000 to about 1,000,000 Daltons and an equivalent weight per primary amine group of about 100 to about 3400 Daltons, wherein the at least one aminated polysaccharide is not chitosan; with (ii) a second solution or dispersion comprising at least one water-dispersible, aldehyde-functionalized multi-arm polyether having at least three arms in a second solvent, wherein at least three of the arms of said multi-arm polyether are terminated by an aldehyde group, said water-dispersible, aldehyde-functionalized multi-arm polyether having a number-average molecular weight of about 450 to about 200,000 Daltons, to form a hydrogel, wherein the first solvent is either the same as or different from the second solvent; and
b) treating the hydrogel to remove at least a portion of said first solvent and said second solvent to form the dried hydrogel.

In another embodiment a method for coating an anatomical site on tissue of a living organism is provided comprising
a) applying to the anatomical site at least one aminated polysaccharide containing primary amine groups, said at least one aminated polysaccharide having a weight-average molecular weight of about 1,000 to about 1,000,000 Daltons and an equivalent weight per primary amine group of about 100 to about 3400 Daltons, wherein the at least one aminated polysaccharide is not chitosan; followed by
b) applying to the anatomical site at least one water-dispersible, aldehyde-functionalized multi-arm polyether having at least three arms wherein at least three of the arms are terminated with an aldehyde group, wherein said water-dispersible, aldehyde-functionalized multi-arm polyether has a number-average molecular weight of about 450 to about 200,000 Daltons; or
c) applying to the anatomical site the polyether of step b) followed by applying to the anatomical site the aminated polysaccharide of step a) and mixing the polyether and the aminated polysaccharide on the anatomical site; or d) premixing the aminated polysaccharide of step a) and the polyether of step b) and applying the resulting mixture to the anatomical site.

In another embodiment, a composition is provided, the composition comprising the reaction product of:

a) at least one aminated polysaccharide containing primary amine groups, said at least one aminated polysaccharide having a weight-average molecular weight of about 1,000 to about 1,000,000 Daltons and an equivalent weight per primary amine group of about 100 to about 3400 Daltons, wherein the at least one aminated polysaccharide is not chitosan; and b) at least one water-dispersible, aldehyde-functionalized multi-arm polyether having at least three arms wherein at least three of the arms are terminated with an aldehyde group, wherein said water-dispersible, aldehyde-functionalized multi-arm polyether has a number-average molecular weight of about 450 to about 200,000 Daltons.

DETAILED DESCRIPTION

As used above and throughout the description of the invention, the following terms, unless otherwise indicated, shall be defined as follows:

The term "aminated polysaccharide containing primary amine groups" refers to a polysaccharide that is derivatized (i.e., chemically modified) to contain primary amine groups.

The term "primary amine group", as used herein, refers to a neutral amino group having two free hydrogens. The amino group may be bound to a primary, secondary or tertiary carbon. As so defined, primary amine group does not include hydrazide groups.

The terms "aminodextran" and "dextran amine" are used interchangeably herein to refer to dextran that has been derivatized (i.e., chemically modified) to contain primary amine groups.

The term "water-dispersible, aldehyde-functionalized multi-arm polyether" refers to a branched polyether, having at least three arms (i.e., branches) wherein at least three of the arms are terminated by an aldehyde group, which is water soluble or able to be dispersed in water to form a colloidal dispersion capable of reacting with a second reactant in aqueous solution or dispersion.

The term "dispersion" as used herein, refers to a colloidal suspension capable of reacting with a second reactant in an aqueous medium.

The term "polyether" refers to a polymer having the repeat unit [—O—R]—, wherein R is a hydrocarbylene group having 2 to 5 carbon atoms. The polyether may also be a random or block copolymer comprising different repeat units which contain different R groups.

The term "hydrocarbylene group" refers to a divalent group formed by removing two hydrogen atoms, one from each of two different carbon atoms, from a hydrocarbon.

The term "branched polyether" refers to a polyether having one or more branch points ("arms"), including star, dendritic, comb, and hyperbranched polyethers.

The term "dendritic polyether" refers to a highly branched polyether having a tree-like structure.

The term "comb polyether" refers to a polyether having a main chain with multiple trifunctional branch points from each of which a linear arm emanates.

The term "star polyether" refers to polyether having a central branch point, which may be a single atom or a chemical group, from which linear arms emanate.

The term "hyperbranched polyether" refers to a highly branched polyether having fewer branches and less regular branching than a dendritic polyether.

The term "equivalent weight per primary amine group" refers to the average molecular weight of the compound divided by the number of primary amine groups in the molecule.

The term "hydrogel" refers to a water-swellable polymeric matrix, consisting of a three-dimensional network of macromolecules held together by covalent or non-covalent crosslinks, that can absorb a substantial amount of water to form an elastic gel.

The term "crosslink" refers to a bond or chain of atoms attached between and linking two different polymer chains.

The term "dried hydrogel" refers to a hydrogel that has been treated to remove substantially all of the solvent contained therein.

The term "% by weight", also referred to herein as wt%, refers to the weight percent relative to the total weight of the solution or dispersion, unless otherwise specified.

The term "PEG" as used herein refers to poly(ethylene glycol).

The term "CMDX" as used herein, refers to carboxymethyldextran.

The term "anatomical site" refers to any external or internal part of the body of humans or animals.

The term "tissue" refers to any tissue, both living and dead, in humans or animals.

By medical application is meant medical applications as related to humans and animals. The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "wt %" means percent by weight, "mol %" means mole percent, "Vol" means volume, "v/v" means volume per volume, "Da" means Daltons, "kDa" means kiloDaltons, the designation "10K" means that a polymer molecule possesses a number-average molecular weight of 10 kiloDaltons, "M" means molarity, "MWCO" means molecular weight cut-off, "kPa" means kilopascals, "$^1$H NMR" means proton nuclear magnetic resonance spectroscopy, "ppm" means parts per million, "PBS" means phosphate-buffered saline.

Disclosed herein is a hydrogel tissue adhesive formed by reacting at least one aminated polysaccharide containing primary amine groups and at least one water-dispersible, aldehyde-functionalized multi-arm polyether. The hydrogel tissue adhesive may be useful as a general tissue adhesive and sealant for medical and veterinary applications including, but not limited to, wound closure, supplementing or replacing sutures or staples in internal surgical procedures such as intestinal anastomosis and vascular anastomosis, tissue repair, ophthalmic procedures, drug delivery, and to prevent post-surgical adhesions. Additionally, due to the presence of the aminated polysaccharide, the hydrogel tissue adhesive disclosed herein may also promote wound healing and blood coagulation, and provide antimicrobial properties.

Aminated Polysaccharides Containing Primary Amine Groups

Aminated polysaccharides useful for preparing the hydrogel tissue adhesive disclosed herein contain primary amine groups. Suitable aminated polysaccharides include, but are not limited to, aminated derivatives of: dextran, carboxymethyldextran, starch, agar, cellulose, hydroxyethylcellulose, carboxymethylcellulose, pullulan, inulin, levan, agarose, and hyaluronic acid. Chitosan is not a suitable aminated polysaccharide because its poor aqueous solubility limits its utility in forming hydrogel tissue adhesives. In one embodiment, the aminated polysaccharide is aminated dextran. In another embodiment, the aminated polysaccharide is aminated carboxymethyldextran. Suitable aminated polysaccharides have a weight-average molecular weight of about 1,000 to about 1,000,000 Daltons, more particularly from about 3,000 to about 250,000 Daltons, and an equivalent weight per primary amine group of about 100 to about 3400 Daltons.

Aminated polysaccharides can be prepared by chemical derivatization of polysaccharides, such as dextran, carboxymethyldextran, starch, agar, cellulose, carboxymethylcellulose, hydroxyethylcellulose, pullulan, hyaluronic acid, and derivatives thereof, using methods known in the art. These polysaccharides are available commercially from sources such as Sigma-Aldrich (Milwaukee, Wis.) and Pharmacosmos A/S (Holbaek, Denmark). Typically, commercial preparations of polysaccharides are a heterogeneous mixture having a distribution of different molecular weights, as well as a variable degree of branching, and are characterized by various molecular weight averages, for example, the weight-average molecular weight ($M_w$), or the number-average molecular weight ($M_n$), as is known in the art. Therefore, the aminated derivatives prepared from these polysaccharides will also have a distribution of different molecular weights. Suitable polysaccharides have a weight-average molecular weight from about 1,000 to about 1,000,000 Daltons, and more particularly from about 3,000 to about 250,000 Daltons.

Aminated polysaccharides can be prepared by oxidizing the desired polysaccharide to introduce aldehyde groups using a suitable oxidizing agent such as periodates, hypochlorites, ozone, peroxides, hydroperoxides, persulfates, or percarbonates. For example, the polysaccharide may be oxidized by reaction with sodium periodate as described by Mo et al. (*J. Biomater. Sci. Polymer Edn.* 11:341-351, 2000). Additionally, the oxidized polysaccharide may be prepared using the method described by Cohen et al. (copending and commonly owned Patent Application No. PCT/US08/05013, WO 2008/133847). That method of making an oxidized polysaccharide comprises a combination of precipitation and separation steps to purify the oxidized polysaccharide formed by oxidation of the polysaccharide with periodate and provides an oxidized polysaccharide with very low levels of iodine-containing species. Then, the oxidized polysaccharide can be reacted with a diamine, such as hexamethylene diamine, ethylene diamine, propylene diamine, and the like, to form Schiff base linkages. Optionally, the Schiff base linkages may be treated with a reducing agent such as sodium borohydride to form stable carbon-nitrogen bonds. Aminated polysaccharides may also be prepared by reacting the polysaccharide with electrophiles such as cyanogen bromide or epichlorohydrin, followed by reaction with a diamine. Alternatively, an amine group may be introduced by the amidation of a carboxyl-containing polysaccharide. Additionally, aminated polysaccharides may be prepared by the methods described by Kirakossian et al. (U.S. Pat. No. 7,179,660, Example A). The amine content of the aminated polysaccharide can be determined using methods known in the art, such as nuclear magnetic resonance spectroscopy (NMR), infrared spectroscopy (IR), or elemental analysis.

Water-Dispersible, Aldehyde-Functionalized Multi-Arm Polyethers

Water-dispersible, aldehyde-functionalized multi-arm polyethers are multi-arm polyethers having the repeat unit [—O—R]—, wherein R is a hydrocarbylene group having 2 to 5 carbon atoms, which have at least three arms terminated with an aldehyde group. Suitable water-dispersible, aldehyde-functionalized multi-arm polyethers have a number-average molecular weight of about 450 to about 200,000 Daltons, more particularly from about 2,000 to about 40,000 Daltons.

Water-dispersible, aldehyde-functionalized multi-arm polyethers include, but are not limited to, dendritic, comb, star, highly branched, and hyperbranched polyethers wherein at least three of the arms are terminated by an aldehyde group. Examples of water-dispersible, aldehyde-functionalized multi-arm polyethers include, but are not limited to, aldehyde-terminated star polyethylene oxides, aldehyde-terminated dendritic polyethylene oxides, aldehyde-terminated comb polyethylene oxides, aldehyde-terminated star polypropylene oxides, aldehyde-terminated dendritic polypropylene oxides, aldehyde-terminated comb polypropylene oxides, aldehyde-terminated star polyethylene oxide-polypropylene oxide copolymers, aldehyde-terminated dendritic polyethylene oxide-polypropylene oxide copolymers, and aldehyde-terminated comb polyethylene oxide-polypropylene oxide copolymers.

Water-dispersible, aldehyde-functionalized multi-arm polyethers may be prepared by derivatizing multi-arm polyethylene glycols (e.g., 3, 4, 6, and 8-arm star polyethylene glycols, available from companies such as Nektar Transforming Therapeutics; SunBio, Inc., Anyang City, South Korea; NOF Corp., Tokyo, Japan; or JenKem Technology USA, Allen, Tex.) to contain terminal aldehyde groups using methods known in the art. For example, primary hydroxy-ended multi-arm polyethers may be converted to toluenesulfonate ends, reacted with sodium hydrosulfide to give thiol ends and subsequently reacted with 3-chloropropionaldehyde diethyl acetal followed by hydrolysis to give thiol-linked aldehyde ends (Harris et al., *ACS Polymer Preprints* 32:154 (1991)). Another polyether aldehyde synthesis is described by Harris (*Poly(Ethylene Glycol) Chemistry: Biotechnical and Biomedical Applications*, J. Milton Harris, Ed., Plenum Press, NY, 1992, Chapter 22). Baudys et al. (U.S. Pat. No.6,465, 694) also describe methods that can be used for preparing polyether aldehydes. Alternatively, an aldehyde-functionalized multi-arm polyether can be prepared by reacting primary hydroxy-ended multi-arm polyethers with thionyl chloride to give a polyether having chloride ends, reacting the chloride-ended polyether with 1-thioglycerol in the presence of a base to yield a thiomethylethyleneglycol-functionalized polyether, which is subsequently oxidized with an oxidizing agent such as periodate to give a thiomethylaldehyde polyether, as described in detail in the Reagent Preparation section of the Examples herein. Additionally, aldehyde-functionalized multi-arm polyethers are available from commercial sources, such as Nektar Transforming Therapeutics.

In one embodiment, the aldehyde-functionalized multi-arm polyether is a four-arm PEG tetra(thiomethylaldehyde), an eight-arm PEG octa(thiomethylaldehyde), or an eight-arm PEG octa-aldehyde.

It should be recognized that the water-dispersible, aldehyde-functionalized multi-arm polyethers are generally a somewhat heterogeneous mixture having a distribution of arm lengths and in some cases, a distribution of species with different numbers of arms. When an aldehyde-functionalized multi-arm polyether has a distribution of species having different numbers of arms, it can be referred to based on the average number of arms in the distribution. For example, in one embodiment the aldehyde-functionalized multi-arm polyether is an aldehyde-functionalized, 8-arm star PEG, which comprises a mixture of aldehyde-functionalized, multi-arm PEGs, some having less than and some having more than 8 arms; however, the aldehyde-functionalized, multi-arm PEGs in the mixture have an average of 8 arms. Therefore, the terms "8-arm", "6-arm", "4-arm" and "3-arm" as used herein to refer to aldehyde-functionalized, multi-arm polyethers, should be construed as referring to a heterogeneous mixture having a distribution of arm lengths and in some cases, a distribution of species with different numbers of arms, in which case the number of arms recited refers to the average number of arms in the mixture.

In one embodiment, the aminated polysaccharide is aminated dextran and the water-dispersible, aldehyde-functionalized multi-arm polyether is a four-arm PEG tetra(thiomethylaldehyde), an eight-arm PEG octa (thiomethylaldehyde), or an eight-arm PEG octa-aldehyde.

In another embodiment, the aminated polysaccharide is aminated carboxymethyldextran and the water-dispersible, aldehyde-functionalized multi-arm polyether is an eight-arm PEG octa-aldehyde.

Methods of Using the Hydrogel Tissue Adhesive

The hydrogel tissue adhesive disclosed herein may used in various forms to form a coating on an anatomical site on tissue of a living organism or to bond at least two anatomical sites together. In one embodiment, the aminated polysaccharide containing primary amine groups and the water-dispersible, aldehyde-functionalized multi-arm polyether are components of aqueous solutions or dispersions. To prepare an aqueous solution or dispersion comprising an aminated polysaccharide (referred to herein as the "first aqueous solution or dispersion"), at least one aminated polysaccharide is added to water to give a concentration of 5% to about 50% by weight, more particularly about 10% to about 40% by weight, relative to the total weight of the solution or dispersion. Mixtures of different aminated polysaccharides, having different backbones, different average molecular weights and/or different equivalent weights per primary amine group, may also be used. If a mixture of different aminated polysaccharides is used, the total concentration of the aminated polysaccharides is about 5% to about 50% by weight, more particularly about 10% to about 40% by weight, relative to the total weight of the solution or dispersion. Similarly, to prepare an aqueous solution or dispersion comprising a water-dispersible, aldehyde-functionalized multi-arm polyether (referred to herein as the "second aqueous solution or dispersion"), at least one water-dispersible, aldehyde-functionalized multi-arm polyether is added to water to give a concentration of about of 5% to about 50% by weight, more particularly about 10% to about 50% by weight, relative to the total weight of the solution or dispersion. Mixtures of different water-dispersible, aldehyde-functionalized multi-arm polyethers, having different backbones, different average molecular weights and/or different numbers of arms, may also be used. If a mixture of different water-dispersible, aldehyde-functionalized multi-arm polyethers is used, the total concentration of the water-dispersible, aldehyde-functionalized multi-arm polyethers is about 5% to about 50% by weight, more particularly about 10% to about 50% by weight, relative to the total weight of the solution or dispersion. The optimal concentrations of the two aqueous solutions or dispersions depends on the intended application, and can be readily determined by one skilled in the art using routine experimentation.

For use on living tissue, it is preferred that the first aqueous solution or dispersion and the second aqueous solution or dispersion be sterilized to prevent infection. Any suitable sterilization method known in the art that does not degrade the components may be used. For example the first aqueous solution or dispersion comprising at least one aminated polysaccharide may be sterilized using heat, ethylene oxide sterilization, ultra-violet radiation, or ultra-filtration through a 0.2 μm pore membrane. The second aqueous solution or dispersion may be sterilized using heat, electron beam irradiation, gamma irradiation, ethylene oxide sterilization, ultra-violet radiation, or ultra-filtration through a 0.2 μm pore membrane.

The first aqueous solution or dispersion and/or the second aqueous solution or dispersion may further comprise various additives depending on the intended application. Preferably, the additive should be compatible with the components of the solution or dispersion. Specifically, the additive does not contain groups that would interfere with effective gelation of the hydrogel. The amount of the additive used depends on the particular application and may be readily determined by one skilled in the art using routine experimentation. For example, the first aqueous solution or dispersion and/or the second aqueous solution or dispersion may comprise at least one additive selected from the group consisting of pH modifiers, viscosity modifiers, antimicrobials, colorants, surfactants, pharmaceutical drugs and therapeutic agents.

The aqueous solution(s) or dispersion(s) may optionally include at least one pH modifier to adjust the pH. Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The aqueous solution(s) or dispersion(s) may optionally include at least one thickener. The thickener may be selected from among known viscosity modifiers, including, but not limited to, polysaccharides and derivatives thereof, such as starch or hydroxyethyl cellulose.

The aqueous solution(s) or dispersion(s) may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The aqueous solution(s) or dispersion(s) may also optionally include at least one colorant to enhance the visibility of the solution(s). Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No.2; and natural colorants such as beetroot red, canthaxanthin, chlorophyll, eosin, saffron, and carmine.

The aqueous solution(s) or dispersion(s) may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the aqueous solution(s) or dispersion(s) may optionally include at least one pharmaceutical drug or therapeutic agent. Suitable drugs and therapeutic agents are well known in the art (for example see the *United States Pharmacopeia* (USP), *Physician's Desk Reference* (Thomson Publishing), *The Merck Manual of Diagnosis and Therapy* 18th ed., Mark H. Beers and Robert Berkow (eds.), Merck Publishing Group, 2006; or, in the case of animals, *The Merck Veterinary Manual*, 9th ed., Kahn, C. A. (ed.), Merck Publishing Group, 2005). Nonlimiting examples include, but are not limited to, anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; anti-coagulants such as heparin; peptides; antibacterial agents; antiviral agents; antifungal agents; anti-cancer agents; healing promoters; vaccines; and thrombogenic agents, such as thrombin, fibrinogen, homocysteine, and estramustine; radio-opaque compounds, such as barium sulfate and gold particles and radiolabels.

The aqueous solution or dispersion comprising at least one aminated polysaccharide and the aqueous solution or dispersion comprising at least one water-dispersible, aldehyde-functionalized multi-arm polyether may be used to apply a coating to an anatomical site on tissue of a living organism in any number of ways. Once both solutions or dispersions are applied to a site, they crosslink to form a hydrogel, a process referred to herein as curing, typically in about 2 seconds to about 2 minutes.

In one embodiment, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In another embodiment, the two aqueous solutions or dispersions are mixed manually before application to the site. The resulting mixture is then applied to the site before it completely cures using a suitable applicator, as described above.

In another embodiment, the two aqueous solutions or dispersions are contained in separate barrels of a double-barrel syringe. In this way the two aqueous solutions or dispersions are applied simultaneously to the site with the syringe. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47). Additionally, the double barrel syringe may contain a motionless mixer, such as that available from ConProtec, Inc. (Salem, N.H.) or Mixpac Systems AG (Rotkreuz, Switzerland), at the tip to effect mixing of the two aqueous solutions or dispersions prior to application. Alternatively, the mixing tip may be equipped with a spray head, such as that described by Cruise et al. in U.S. Pat. No. 6,458,147. Additionally, the mixture of the two aqueous solutions or dispersions from the double-barrel syringe may be applied to the site using a catheter or endoscope. Devices for mixing a two liquid component tissue adhesive and delivering the resulting mixture endoscopically are known in the art and may be adapted for the mixing and delivery of the two aqueous solutions or dispersions disclosed herein (see for example, Nielson, U.S. Pat. No. 6,723,067; and Redl et al., U.S. Pat. No. 4,631,055).

In another embodiment, the first aqueous solution or dispersion and the second aqueous solution or dispersion are applied to the site simultaneously where they mix to form a hydrogel. The two aqueous solutions or dispersions may be applied to the site in various ways, for example, using a dual-lumen catheter, such as those available from Bistech, Inc. (Woburn, Mass.). Additionally, injection devices for introducing two liquid components endoscopically into the body simultaneously are known in the art and may be adapted for the delivery of the two aqueous solutions or dispersions disclosed herein (see for example, Linder et al., U.S. Pat. No. 5,322,510).

In another embodiment, the two aqueous solutions or dispersions may be applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862).

In another embodiment, the two aqueous solutions or dispersions may be applied to the site using a minimally invasive surgical applicator, such as those described by Sawhney (U.S. Pat. No. 7,347,850).

In another embodiment, the hydrogel tissue adhesive of the invention is used to bond at least two anatomical sites together. In this embodiment, the aqueous solution or dispersion comprising the aminated polysaccharide is applied to at least one anatomical site, and the aqueous solution or dispersion comprising the water-dispersible, aldehyde-functionalized multi-arm polyether is applied to at least one of either the same site or one other site using the methods described above. The two or more sites are contacted and held together manually or using some other means, such as a surgical clamp, for a time sufficient for the mixture to cure, typically from about 2 seconds to about 2 minutes. Alternatively, a mixture of the two aqueous solutions or dispersions is applied to at least one of the anatomical sites to be bonded using methods described above. The two or more sites are contacted and held together manually or using some other means, such as a surgical clamp, for a time sufficient for the mixture to cure.

In another embodiment, the aminated polysaccharide and the water-dispersible, aldehyde-functionalized multi-arm polyether are used in the form of finely divided powders. The powders may be prepared using any suitable method. For example, the aqueous solutions described above may be dried using heat, vacuum, a combination of heat and vacuum, or by lyophilization, to form powders. Optionally, the powders may be comminuted into finer particles using methods known in the art including, but not limited to, grinding, milling, or crushing with a mortar and pestle. The finely divided powders may be sterilized using the methods described above. The finely divided powders may be applied to an anatomical site on tissue of a living organism in a variety of ways. For example, the powders may be individually applied to the site in any order by sprinkling or spraying. Additionally, the two powders may be premixed and the resulting mixture applied to the site using the methods described above. The powders may be hydrated on the site by the addition of a suitable buffer (e.g., phosphate-buffered saline) or by the physiological fluids present at the site. The finely divided powders may also be used to bond two anatomical sites together as described above for the aqueous solutions or dispersions.

In another embodiment, the hydrogel tissue adhesive disclosed herein is used in the form of a dried hydrogel. In this embodiment, a hydrogel is prepared by mixing a solution or dispersion comprising at least one aminated polysaccharide in a first solvent with a solution or dispersion comprising at least one water-dispersible, aldehyde-functionalized multi-arm polyether in a second solvent to form a hydrogel. The first solvent may be either the same as or different from the second solvent. If two different solvents are used to prepare the first solution or dispersion and the second solution or dispersion, the two solvents are miscible with each other. Suitable solvents include, but are not limited to, water, ethanol, isopropanol, tetrahydrofuran, hexanes, polyethylene glycol, and mixtures thereof. In one embodiment, both the first solvent and the second solvent are water. The solutions or dispersions may further comprise various additives depending on the intended application. Any of the additives described above may be used. The hydrogel is then treated to remove at least a portion of the solvent(s) contained therein to form the dried hydrogel. Preferably, substantially all of the solvent(s) is/are removed from the hydrogel. The solvent(s) may be removed from the hydrogel using methods known in the art, for example, using heat, vacuum, a combination of heat and vacuum, or flowing a stream of dry air or a dry inert gas such as nitrogen over the hydrogel. The dried hydrogel may be sterilized using the methods described above.

In one embodiment, the dried hydrogel is used in the form of a film. The dried hydrogel film may be formed by casting a mixture of the two solutions or dispersions on a suitable substrate and treating the resulting hydrogel to form a dried hydrogel film. The dried hydrogel film may be applied directly to an anatomical site. Additionally, the dried hydrogel film may be used to bond two anatomical sites together.

In another embodiment, the dried hydrogel is used in the form of finely divided particles. The dried hydrogel particles may be formed by comminuting the dried hydrogel using methods known in the art, including, but not limited to, grinding, milling, or crushing with a mortar and pestle. The dried hydrogel particles may be applied to an anatomical site in a variety of ways, such as sprinkling or spraying, and may also be used to bond two anatomical sites together.

Kits

In one embodiment, the invention provides a kit comprising at least one aminated polysaccharide containing primary amine groups and at least one water-dispersible, aldehyde-functionalized multi-arm polyether, as described above, provided that the aminated polysaccharide is not chitosan.

In another embodiment, the kit comprises at least one aminated polysaccharide contained in a first aqueous solution or dispersion and at least one water-dispersible, aldehyde-functionalized multi-arm polyether in a second aqueous solution or dispersion, as described above. Each of the aqueous solutions or dispersions may be contained in any suitable vessel, such as a vial or a syringe barrel.

In another embodiment, the kit comprises at least one aminated polysaccharide and at least one water-dispersible, aldehyde-functionalized multi-arm polyether in the form of finely divided powders, as described above. The powders may be contained in separate containers or they may be premixed and contained in a single container. The kit may also comprise a buffer solution for hydrating the powders.

In another embodiment, the kit comprises a dried hydrogel formed by reacting at least one aminated polysaccharide with at least one water-dispersible, aldehyde-functionalized multi-arm polyether, as described above. The dried hydrogel may be in the form of a film, finely divided particles, or other dried forms. The kit may further comprise a buffer for hydrating the dried hydrogel. The dried hydrogel may be contained in any suitable container.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

A reference to "Aldrich" or a reference to "Sigma" means the said chemical or ingredient was obtained from Sigma-Aldrich, St. Louis, Mo.

The water used in the following Examples was deionized, unless otherwise stated.

Reagent Preparation

Preparation of Aminated Dextran Having an Equivalent Weight per Primary Amine Group of about 247 from Dextran Having a Weight-Average Molecular Weight of 8,500-11,500 Daltons (D10-247 Amine)

Aminated dextran having an equivalent weight per primary amine group of about 247 Daltons is prepared by oxidizing dextran having a weight-average molecular weight of 8,500 to 11,500 Daltons to introduce aldehyde groups using sodium periodate and then reacting the oxidized dextran with hexamethylene diamine. A typical procedure is described here.

A dextran aldehyde with about 50% oxidation conversion (i.e., about half of the glucose rings in the dextran polymer were oxidized to dialdehydes) is prepared from dextran having a weight-average molecular weight of 8,500 to 11,500 Daltons (Sigma). Dextran (19.0 g; 0.12 mol saccharide rings; weight-average molecular weight of 8,500-11,500 Da; Sigma, product number D9260) is added to 170 g of water in a 500 mL round bottom flask. The mixture is stirred for 15 to 30 min to produce a solution; then a solution of 17.7 g (0.083 mol; mw=213.9) sodium periodate in 160 g of water is added to the dextran solution all at once. The mixture is stirred at room temperature for 5 hours. After this time, the solution is removed from the round bottom flask, divided into four equal volumes and dispensed into 4 dialysis membrane tubes [Molecular weight cut-off (MWCO)=3500 Da]. The tubes are dialyzed in deionized water for 4 days, during which time the water is changed twice daily. The aqueous solutions are removed from the dialysis tubes, placed in wide-mouth polyethylene containers and frozen using liquid nitrogen, and lyophilized to afford white, fluffy oxidized dextran.

The dialdehyde content in the resulting oxidized dextran is determined using the following procedure. The oxidized dextran (0.1250 g) is added to 10 mL of 0.25 M NaOH in a 250 mL Erlenmeyer flask. The mixture is gently swirled and then placed in a temperature-controlled sonicator bath at 40° C. for 5 min until all the material dissolved, giving a dark yellow solution. The sample is removed from the bath and the flask is cooled under cold tap water for 5 min. Then 15.00 mL of 0.25 M HCl is added to the solution, followed by the addition of 50 mL of water and 1 mL of 0.2% phenolphthalein solution. This solution is titrated with 0.25 M NaOH to an endpoint determined by a color change from yellow to purple/violet. The same titration is carried out on a sample of the starting dextran to afford a background aldehyde content. The dialdehyde content, also referred to herein as the oxidation conversion or the degree of oxidation, in the oxidized dextran sample is calculated using the following formula:

$$\text{Dialdehyde Content} = \frac{(Vb - Va)_s}{W_s/M} - \frac{(Vb - Va)_p}{W_p/M} \times 100\%$$

Vb=total meq of base
Va=total meq of acid
W=dry sample weight (mg)
M=weight-average molecular weight of dextran repeat unit (162)
s=oxidized sample
p=original sample Alternatively, oxidized dextran is prepared by the method described by Cohen et al. (copending and commonly owned Patent Application No. PCT/US08/05013). A typical procedure is described here.

A 20-L reactor equipped with a mechanical stirrer, addition funnel, internal temperature probe, and nitrogen purge is charged with 1000 g of the dextran and 9.00 L of deionized water. The mixture is stirred at ambient temperature to dissolve the dextran and then cooled to 10 to 15° C. To the cooled dextran solution is added over a period of an hour, while keeping the reaction temperature below 25° C., a solution of 1000 g of sodium periodate dissolved in 9.00 L of deionized water. Once all the sodium periodate solution has been added, the mixture is stirred at 20 to 25° C. for 4 more hours. The reaction mixture is then cooled to 0° C. and filtered to clarify. Calcium chloride (500 g) is added to the filtrate, and the mixture is stirred at ambient temperature for 30 min and then filtered. Potassium iodide (400 g) is added to the filtrate, and the mixture is stirred at ambient temperature for 30 min. A 3-L portion of the resulting red solution is added to 9.0 L of acetone over a period of 10 to 15 min with vigorous stirring by a mechanical stirrer during the addition. After a few more minutes of stirring, the agglomerated product is separated from the supernatant liquid. The remaining red solution obtained by addition of potassium iodide to the second filtrate is treated in the same manner as above. The combined agglomerated product is broken up into pieces, combined with 2 L of methanol in a large stainless steel blender, and blended until the solid becomes granular. The granular solid is recovered by filtration and dried under vacuum with a nitrogen purge. The granular solid is then hammer milled to a fine powder. A 20-L reactor is charged with 10.8 L of deionized water and 7.2 L of methanol, and the mixture is cooled to 0° C. The granular solid formed by the previous step is added to the reactor and the slurry is stirred vigorously for one hour. Stirring is discontinued, and the solid is allowed to settle to the bottom of the reactor. The supernatant liquid is decanted by vacuum, 15 L of methanol is added to the reactor, and the slurry is stirred for 30 to 45 min while cooling to 0° C. The slurry is filtered in portions, and the recovered solids are washed with methanol, combined, and dried under vacuum with a nitrogen purge to give about 600 g of the oxidized dextran. The degree of oxidation of the product is determined using the titration method described above or by proton NMR. In the NMR method, the integrals for two ranges of peaks are determined, specifically, —O$_2$CHx- at about 6.2 parts per million (ppm) to about 4.15 ppm (minus the HOD peak) and —OCHx- at about 4.15 ppm to about 2.8 ppm (minus any methanol peak if present). The calculation of oxidation level is based on the calculated ratio (R) for these areas, specifically, R=(OCH)/(O$_2$CH).

The dextran aldehyde described above (5g) is dissolved in 500 mL of 0.1 M borate buffer, pH 11.0. The dextran aldehyde solution is added slowly over 5 hours using a syringe pump to a basic solution of hexamethylene diamine (36 g) dissolved in 296 mL of deionized water. The mixture is stirred at room temperature for 24 hours, after which time sodium borohydride (4 g) is added, and the reaction mixture is stirred for another 24 hours. Another aliquot of sodium borohydride (4 g) is added, and the reaction mixture is stirred for another 24 hours. The resulting solution is filtered using a Millipore Pellicon II TFF system (Millipore Corp., Billerica, Mass.) with a 1000 Da MWCO, regenerated cellulose membrane. The solution is first concentrated to a volume of 1000 mL, then a 12× volume of waste is collected, and then the resulting solution is lyophilized to dryness to yield the aminated dextran, referred to herein as D10-247 amine, as a white solid.

$^1$H NMR: $^1$H NMR (D$_2$O): 1.40 ppm, 1.54 ppm, 1.64 ppm (sum of integral of 1.40-1.64 ppm: 11.42), 2.3-2.96 ppm (broad, integral 7.7), 3.57-3.93 ppm (broad multiplet, integral 10.70), 4.98 ppm (broad, anomeric proton, integral 1.72).

Preparation of Aminated Dextran Having an Equivalent Weight per Primary Amine Group of about 490 from Dextran Having a Weight-Average Molecular Weight of 8,500-11,500 Daltons (D10-490 Amine)

Dextran aldehyde with about 20% oxidation conversion is prepared from dextran having a weight-average molecular weight of 8,500 to 11,500 Daltons (Sigma) using either of the methods described above. The amount of periodate used is adjusted to give the desired oxidation conversion.

The dextran aldehyde with about 20% oxidation conversion (5 g) is dissolved in 500 mL of 0.1 M borate buffer, pH 11. The dextran aldehyde solution is added slowly over 5 hours using a syringe pump to a basic solution containing 15 g of hexamethylene diamine dissolved in 296 mL of deionized water. The mixture is stirred at room temperature for 24 hours, after which time sodium borohydride (4 g) is added, and the reaction mixture is stirred for another 24 hours. Another aliquot of sodium borohydride (4 g) is added, and the reaction mixture is stirred for another 24 hours. The resulting solution is filtered using a Millipore Pellicon II TFF system, as described above. The solution is first concentrated to a volume of 1000 mL, then a 12× volume of waste is collected, and resulting solution is lyophilized to dryness to yield the aminated dextran, referred to herein as D10-490 amine.

1H NMR: $^1$H NMR (D$_2$O): 1.40 ppm, 1.54 ppm, 1.64 ppm (sum of integral of 1.40-1.64 ppm: 2.15), 2.3-2.96 ppm (broad, integral 1.24), 3.53-3.58 (multiplet, integral 2.00), 3.90-4.00 ppm (multiplet, integral 2.25), 4.98 ppm (broad, anomeric proton, integral 1.0).

Preparation of Four-Arm PEG 2K Tetra(thiomethylaldehyde) (P4-2-1-SCH$_2$CHO)

A 4-arm PEG 2K (M$_n$~2,000 Da) tetra(thiomethylaldehyde) is prepared by reacting 4-arm PEG 2K tetrachloride with 1-thioglycerol to give a 4-arm PEG 2K with thiomethylethyleneglycol ends. Oxidation of this intermediate with one equivalent of sodium metaperiodate per glycol group yields the 4-arm PEG 2K terminated with thiomethylaldehyde groups. A typical preparation is described here.

The 4-arm PEG 2K tetrachloride is prepared by reacting a four-arm PEG 2K tetraalcohol with thionyl chloride. Four-arm PEG 2K tetraalcohol (M$_n$=2000; NOF SunBright PTE-2000), (100 g in a 500-mL round-bottom flask) is dissolved in 100 mL of dichloromethane. Thionyl chloride (88 mL, 1.2 mol) is added, and the mixture is stirred under a blanket of nitrogen at ambient temperature for 24 hours. Excess thionyl chloride and dichloromethane are removed by rotary evaporation (bath temp 40° C.). Two successive 50-mL portions of toluene are added and evaporated under reduced pressure (2 kPa, bath temperature 60° C.) to complete the removal of thionyl chloride.

A solution of 10.1 g of the 4-arm PEG 2K tetrachloride, 2.52 g of sodium bicarbonate, and thioglycerol (Aldrich, 5 g) in 75 mL of deionized water is stirred in a 90° C. oil bath under nitrogen for 14 hours. The solution is cooled to room temperature and is extracted with three 35 mL portions of dichloromethane. The combined extracts are dried with sodium sulfate followed by magnesium sulfate, filtered, concentrated to 25 mL, and added to 500 mL of diethyl ether in an Erlenmeyer flask. The mixture is stirred for 15 min and then cooled in dry ice to freeze the product. The ether is decanted off, replaced with 100 mL of fresh ether and the mixture is warmed to room temperature and stirred for 10 min, followed by freezing and decanting again. The product is then taken up in 25 mL of dichloromethane and transferred to a 100-mL round-bottom flask. The Erlenmeyer flask is rinsed with 10 mL of dichloromethane, which is then added to the solution in the round-bottom flask. The solution is rotary evaporated from a warm tap water bath (release vacuum under nitrogen), and then maintained under high vacuum at room temperature for a few hours (release vacuum under nitrogen), to yield a yellow oil product (10.48 g).

The resulting oil (10 g) is dissolved in 100 mL of deionized water, and cooled in an ice bath. A solution of sodium periodate (3.72 g) in 50 mL of water is added using an addition funnel over a period of 45 min. The mixture is stirred for 60 min at 0-5° C. and then ethylene glycol (9.72 g) is added. The solution is warmed to room temperature, and extracted four times with 150 mL portions of dichloromethane. The combined extracts are dried with magnesium sulfate and concentrated by rotary evaporation from a warm tap water bath to a volume of about 15 mL. The resulting concentrate is added with stirring to 500 mL of diethyl ether in an Erlenmeyer flask. The mixture is stirred for 15 min and then cooled in dry ice to freeze the product. The ether is decanted off, replaced with 300 mL of fresh ether and the mixture is warmed to room temperature and stirred for 10 min, followed by freezing and decanting again. The product is then taken up in 25 mL of dichloromethane and transferred to a 100-mL round-bottom flask. The Erlenmeyer flask is rinsed with 10 mL of dichloromethane, which is then added to the solution in the round-bottom flask. The solution is rotary evaporated from a warm tap water bath (release vacuum under N2), and then maintained under high vacuum at room temperature for a few hours (release vacuum under N2) to yield the four-arm PEG 2K tetra(thiomethylaldehyde), referred to herein as P4-2-1-SCH$_2$CHO, as a yellow oil.

Preparation of Eight-Arm PEG 10K Thiomethyladehyde (P8-10-1-SCH$_2$CHO)

An 8-arm PEG 10K ($M_n$~10,000) octa(thiomethylaldehyde) is prepared by reacting 8-arm PEG 10K octachloride with 1-thioglycerol to give an 8-arm PEG 10K with thiomethylethyleneglycol ends. Oxidation of this intermediate with one equivalent of sodium metaperiodate per glycol group yields the 8-arm PEG 10K terminated with thiomethylaldehyde groups. A typical preparation is described here.

The 8-arm PEG 10K octachloride is prepared by reacting an 8-arm PEG 10K octaalcohol with thionyl chloride using a procedure similar to that described above for the preparation of the 4-arm PEG 2K tetrachloride. The starting 8-arm PEG 10K octaalcohol is obtained from NOF Corp. (Tokyo, Japan)

A solution of 10.1 g (8 mmol Cl) of the 8-arm PEG 10K octachloride, 1.0 g (12 mmol, mw=84) of sodium bicarbonate and 2.2 g (1.7 mL, 20 mmol) of 1-thioglycerol (mw=108.12; density=1.25; Aldrich, M1753) in 30 mL of water is stirred in a 90° C. oil bath under nitrogen for 14 hours. The solution is cooled to room temperature and is extracted with three 35 mL portions of dichloromethane. The combined extracts are dried with sodium sulfate followed by magnesium sulfate, filtered, concentrated to 25 mL and then precipitated from 500 mL of diethyl ether. Suction filtration under nitrogen yields the 8-arm PEG 10K with thiomethylethyleneglycol ends as a white solid.

A solution of the 8-arm PEG 10K with thiomethylethyleneglycol ends in 80 mL of deionized water is stirred in an ice bath as a solution of sodium periodate in 20 mL of water is added in approximately 3-mL portions every 5 min. The mixture is allowed to stir for 60 min at 0-5° C. and then ethylene glycol is added. The solution is warmed to room temperature, and extracted with four 150 mL portions of dichloromethane. The combined extracts are dried with magnesium sulfate and concentrated on by rotary evaporation from a warm tap water (no heat on hot plate) bath to a volume of about 15 mL. To the resulting solution is added 200 mL of diethyl ether and the solution is frozen on dry ice for 15 min, forming a solid, which is quickly collected cold, and then stirred with ether at room temperature for 10 min. The solid product is a very fine powder that is collected by filtration using a medium porosity fritted funnel. The aqueous filtrate is concentrated to approximately 15 mL under vacuum overnight. The resulting solution is re-extracted with three 150 mL portions of dichloromethane according to the steps described above. A final extraction is made using three 75 mL portions of chloroform, according to the procedure described above. The solids are combined to give the 8-arm PEG 10K octa(thiomethylaldehyde) product, referred to herein as P8-10-1-SCH$_2$CHO.

Preparation of Eight-Arm PEG 10K Octa-Aldehyde (P8-10-1-CHO) by Swern Oxidation

An 8-arm PEG 10K ($M_n$~10,000) octaalcohol (NOF Corp.) is dried under vacuum at 70° C. for 6 hours and stored in a dry box until use (approximately 1 week). A solution containing oxalyl chloride (0.74 g, 0.0058 mol, Aldrich) in anhydrous methylene chloride (100 mL) is placed in a 3 neck oven-dried flask, equipped with a stir bar, thermometer, and two addition funnels under nitrogen. One addition funnel contains anhydrous dimethylsulfoxide (DMSO, 0.98 mL) in 30 mL of methylene chloride. The other additional funnel contains the 8-arm PEG 10K octaalcohol (6 g, 0.0048 mol) in methylene chloride (20 mL). The flask is cooled to −45° C. and the DMSO solution is added dropwise, keeping the temperature below −35° C. Stirring is continued at −45° C. for another 30 min, followed by the dropwise addition of the 8-arm PEG 10K octaalcohol solution, while keeping the temperature below −35° C. The reaction mixture is stirred for another 30 min at −45° C. Triethylamine (2.42 g) is then added dropwise at −45° C., and the mixture is stirred for 30 min at −60° C. in an acetone/dry ice bath. After this time, the cooling bath is removed, and the reaction mixture is warmed to 10° C. Then, 20 mL of water is added to the reaction mixture and the mixture is stirred for 30 min. The resulting layers are separated, and the aqueous layer is extracted with three 30 mL portions of methylene chloride. The organic layers from the three extractions are combined, dried over sodium sulfate, and filtered twice through a 2 inch (5 cm) pad of Celite® diatomaceous earth (World Minerals, Lompoc, Calif.). The solvent is removed under reduced pressure. The product is then precipitated by dissolving in a minimal volume of dichloromethane (approximately 20 mL) and adding 100 mL of ether. The solution is chilled in an ice/brine bath until a white precipitate forms. The precipitation is repeated, and the product is filtered and washed twice with 30 mL of ether. The product is dried under reduced pressure to yield the 8-Arm PEG 10K aldehyde, referred to herein as P8-10-1-CHO, as a white solid.

Preparation of 60 kDa Aminoethylamido-Carboxymethyldextran Having a Degree of Carboxymethylation of 1.8 and an Equivalent Weight per Primary Amine Group of About 428 Da (CMDX-60-428 Amine)

The aminoethylamido carboxymethyl dextran is prepared using a two step process. In the first step carboxymethyldextran is prepared by reacting dextran with chloroacetic acid. This step is repeated to obtain the desired level of carboxymethylation. The resulting carboxymethyldextran is reacted with 1-BOC (i.e., t-butoxycarbonyl) ethylenediamine, after activation of the carboxymethyl group with 1-ethyl-3-(3-dimethylaminopropyl) carbodiimide hydrochloride (EDC). A typical procedure is describe here.

To a solution containing 20 g of dextran having a weight-average molecular weight of 60 to 90 kDa (Sigma) in 165 mL of 6 N NaOH at 0° C. is added 41 g of chloroacetic acid. The temperature of the solution is then raised to 60° C. for 20 min while stirring the solution. The mixture is rapidly cooled and neutralized to pH 7.0 with 6 N HCl. The product is precipitated by slow addition of the reaction solution to 1.0 L of methanol with vigorous stirring. The white solid is collected by filtration, resuspended in 200 mL of water and re-precipitated. The resulting solid is dried in a vacuum oven at 80° C. overnight to a white powder. The degree of carboxymethylation is determined by the method of Ho et al. (*Anal. Chem.* 52:916, 1980) to be 0.91. This carboxymethyldextran product is referred to herein as CMDX-60-0.91.

CMDX-60-0.91 (13 g) is dissolved in 107 mL of 6 N NaOH and cooled to 0° C. in an ice bath. The cooled solution is stirred while 26.6 g of chloroacetic acid is added, and the resulting mixture is heated to 60° C. for 20 min. The solution is rapidly cooled and pH adjusted to 7.0 by addition of concentrated HCl. The product is isolated by precipitation from methanol twice, followed by drying in a vacuum oven at 60° C. overnight. The degree of carboxymethylation is further increased by repeating the procedure with this product by dissolving 14.8 g in 122 mL of 6 N NaOH and cooling to 0° C. in an ice bath. The cooled solution is stirred while 30.31 g of chloroacetic acid is added, and the resulting mixture is heated to 60° C. for 20 min. The solution is rapidly cooled and pH adjusted to 7.0 by addition of concentrated HCl. The solution is diafiltered using a Millipore Pellicon II TFF system (Millipore Corp., Billerica, Mass.) using three 0.1 m², 1 kDa MWCO filters in series. A total of 6 volumes of permeate are collected while continuously adding water to maintain a constant retentate volume. The retentate is then collected and lyophilized to give a fluffy white solid. The degree of carboxymethylation is determined by the method of Ho et al., supra to be 1.80. This carboxymethyldextran product is referred to herein as CMDX-60-1.80.

To a 1-L, 3-neck flask is added 4.5 g of CMDX-60-1.80 and 301 mL of 1:1 mixture of 10 mM of N,N,N'N', tetramethylethylene diamine (TMED) (pH 4.7) and dimethylformamide (DMF). The mixture is stirred for 5 min to form a clear solution and then 15.7 g of 1-ethyl-3-(3-dimethylaminopropyl) carbodiimide hydrochloride (EDC), obtained from Sigma, is added, followed by 9.4 g of N-hydroxysuccinimide (NHS), obtained from Aldrich. The solution is stirred under nitrogen for 2.5 h, after which time the pH dropped to 3.45. To the solution is then added 13.11 g of 1-BOC-ethylenediamine (Combi-Blocks Inc., San Diego, Calif.) in portions over a 2.5 hour period at a rate at which the pH did not exceed 4.7. The pH of the reaction mixture initially increases upon addition of the BOC-amine, and then decreases slightly after stirring for a few minutes. When the addition is completed, the final pH is 5.63. Then, 0.25 N NaOH is added to raise the pH to 6.5. The reaction mixture is stirred magnetically at room temperature overnight. Then, the reaction mixture is transferred to a 1-L glass jar and diluted to 1.0 L with water. The volume is reduced to 400 mL using the Millipore Pellicon II system described above. The solution is then diafiltered using water to replace the collected permeate until 5× the starting volume has been collected. An additional 5× volume is collected after adjusting the pH to 3.0 with dilute HCl and replacing the permeate with 0.001M HCl. The retentate solution is then adjusted to pH 7.0 and diafiltered, collecting an additional 5× permeate with replacement by water. The final retentate solution is reduced to 300 mL, then the lines are washed with 200 mL of water. The combined retentate is lyophilized to give a white powder.

The entire procedure is then repeated using 4.85 g of the white powder product using the same amounts of solvent, EDC and NHS, to increase the amine substitution. A white solid is recovered.

The BOC protecting group is removed using the following procedure to give the aminoethylamido-carboxymethyldextran. The white solid product (2.1 g) is treated with 30 mL of 70% aqueous trifluoroacetic acid (TFA) for 2 hours, then diluted with 200 mL of water and pH adjusted to 8.0 with 6 N NaOH. The solution is diafiltered using a Millipore Pellicon II system, as described above, replacing the permeate with 0.01 M HCl until 5 volumes of permeate have been collected. Then, diafiltration is continued while replacing the next 5 volumes with 0.1 M NaCl, and then by an additional 5 volumes with water. Finally, the pH is adjusted to 8.0 with 6 N NaOH and filtration is continued until the permeate is pH 7.0. The sample is lyophilized to give the aminoethylamido-carboxymethyldextran as a white solid. The amine substitution of the product is determined to be 61% using $^1$H NMR in $D_2O$. The aminoethylamido-carboxymethyldextran is referred to herein as CMDX-60-428 amine.

Examples 1-5

In Vitro Biocompatibility Testing—Cytotoxicity

The following Examples demonstrate the safety of hydrogels resulting from the reaction of an aminated dextran with an aldehyde-functionalized multi-arm PEG.

The testing was done using NIH3T3 mouse fibroblast cell cultures according to ISO10993-5:1999. The NIH3T3 mouse fibroblast cells were obtained from the American Type Culture Collection (ATCC; Manassas, VA) and were grown in Dulbecco's modified essential medium (DMEM), supplemented with 10% fetal calf serum.

NIH3T3 mouse fibroblast cell cultures were challenged with hydrogels made by combining equal volumes of an aqueous solution containing an aldehyde-functionalized multi-arm PEG and an aqueous solution containing an aminodextran, as shown in Table 1. Each hydrogel was placed in the bottom of a well in a polystyrene culture plate such that about ¼ of the well bottoms were covered. The wells were then sterilized under UV light and seeded with 50,000-100,000 NIH3T3 cells.

The cells grew normally confluent and coated the well bottom, growing up to the edges of the hydrogels; however, they did not overgrow the hydrogels. These results, summarized in Table 1, demonstrate a lack of cytotoxicity of the hydrogels, as well as the lack of adhesion of cell cultures to the hydrogels.

TABLE 1

| | Cytotoxicity Results | | |
|---|---|---|---|
| Example | PEG Aldehyde Solution | Aminodextran Solution | Cytotoxicity |
| 1 | P8-10-1-CHO (Swern) 30 wt % | D10-247 amine 10 wt % | nontoxic |
| 2 | P8-10-1-SCH$_2$CHO 50 wt % | D10-247 amine 20 wt % | nontoxic |
| 3 | P4-2-1-SCH$_2$CHO 50 wt % | D10-247 amine 10 wt % | nontoxic |
| 4 | P4-2-1-SCH$_2$CHO 50 wt % | D10-247 amine 20 wt % | nontoxic |

TABLE 1-continued

Cytotoxicity Results

| Example | PEG Aldehyde Solution | Aminodextran Solution | Cytotoxicity |
|---|---|---|---|
| 5 | P8-10-1-SCH$_2$CHO 50 wt % | D10-490 amine 10 wt % | nontoxic |

Examples 6-8

In-Vitro Burst Testing of a Sealed Scalpel Incision

The following Examples demonstrate the burst strength of a seal made with various hydrogels of an incision made in swine uterine horn.

A syringe pump system was used to measure the burst strength of a seal of an incision made in a section of swine uterine horn. The syringe pump (Model No. 22, Harvard Apparatus, Holliston, Mass.) was modified to be equipped with two 30 mL syringes, which were connected together through a "Y" junction. Water was pumped through a single piece of Tygon® R-36 tubing (0.6 cm diameter) and through a pressure gauge (Model PDG 5000L, Omega Engineering, Stamford, Conn.).

An approximately 12.5 cm section of clean swine uterine horn, obtained from a local abattoir, was fitted on one end with a metal plug with a feed line fitting for water feed from the syringe pump and on the other end with a metal plug with a threaded hole which could be sealed with a machine screw. The plugs were held in place with nylon ties around the outside of the uterine horn. An incision was made through the uterine horn wall into the interior by puncturing with a Bard Parker™ surgical blade handle 5 (obtained from BD Surgical Products, Franklin Lakes, N.J.), fitted with a #15 surgical blade. The incision on the outside of the uterine horn was wider than the scalpel blade (typically 4-5 mm) while the hole through the inside wall was about 3 mm (about equal to the blade). This size incision mimics the distance between the interrupted sutures if an intestine were to be cut and later sutured. The uterine horn was filled with water containing a purple dye via the syringe pump until water began to leak from the open hole in the end plug and also from the scalpel puncture in the intestinal wall. The pump was then turned off and the end plug was sealed with the machine screw. The scalpel incision site was blotted dry using a paper towel.

The aldehyde-functionalized multi-arm PEG and aminodextran solutions were prepared in water. The two solutions were applied to the incision using a double barrel syringe (Mixpac Systems AG (Rotkreuz, Switzerland) fitted with a 16 step static mixer (Mixpac Systems AG). After the application, the adhesive was allowed to cure at room temperature for no longer than 2 min.

Burst pressure testing, also referred to herein as leak pressure testing, was done by pressurizing the sealed uterine horn with water from the syringe pump at a flow rate of 11 mL/min until the bioadhesive seal began to leak, at which point the pressure was recorded. Adhesive failure was attributed when the water leaked under the seal between the hydrogel and the tissue surface. Cohesive failure was attributed when the water penetrated and leaked through the hydrogel itself. Burst pressure testing was also done on the unsealed uterine horn and the leak pressure was less than 10 mm of mercury (Hg) (less than 1.3 kPa).

The results of the burst testing are summarized in Table 2. The results demonstrate the hydrogels formed by reaction of various aldehyde-functionalized multi-arm PEGs and aminodextran solutions were able to seal the incision in the swine uterine horn.

TABLE 2

Burst Pressure Testing Results

| Example | PEG Aldehyde Solution | Aminodextran Solution | Ave Burst Pressure, mm Hg |
|---|---|---|---|
| 6 | P8-10-1-SCH$_2$CHO 50 wt % | D10-247 amine 20 wt % | 236 (31.5 kPa) |
| 7 | P8-10-1-SCH$_2$CHO 50 wt % | D10-490 amine 10 wt % | 67 (8.9 kPa) |
| 8 | P8-10-1-CHO (Swern) 40 wt % | D10-247 amine 10 wt % | 34 (4.5 kPa) |

Examples 9-11

In Vitro Degradation of Hydrogels

The following Examples demonstrate that the hydrogels formed by reaction of an aldehyde-functionalized multi-arm PEG with an aminodextran have low swell and persist for prolonged periods of time in vitro.

The hydrogel samples were prepared by mixing equal volumes of an aqueous solution of a multi-arm PEG aldehyde and an aqueous solution of an aminodextran using a double barrel syringe (Mixpac Systems AG (Rotkreuz, Switzerland) fitted with a 16 step static mixer (Mixpac Systems AG), as shown in Table 3. After the hydrogels cured, the samples were weighed and placed inside jars containing phosphate-buffered saline (PBS). The jars were placed inside a temperature-controlled shaker set at 80 rpm and 37° C. The samples were removed from the jars at various times, blotted to remove excess solution, and weighed. Then, the samples were returned to the jars.

The results are summarized in Table 3. The percent swell reported in the table is the weight of the hydrogel at the specified time divided by the initial weight of the hydrogel, multiplied by 100. All of the hydrogels were still present after 13 days (312 h). The results indicate that the hydrogels have low swell and persist for long periods of time.

TABLE 3

Results of In Vitro Degradation of Hydrogels

| Example | PEG Aldehyde Solution | Aminodextran Solution | % Swell 6 h | 24 h | 72 h | 192 h |
|---|---|---|---|---|---|---|
| 9 | P8-10-1-SCH$_2$CHO 50 wt % | D10-247 amine 20 wt % | 193 | 197 | 200 | 200 |
| 10 | P8-10-1-SCH$_2$CHO 50 wt % | D10-490 amine 10 wt % | 157 | 156 | 152 | 156 |
| 11 | P8-10-1-CHO (Swern) 40 wt % | D10-247 amine 10 wt % | 283 | 265 | 217 | 203 |

EXAMPLE 12

In Vitro Degradation of Hydrogels formed from Aminated Carboxymethyldextran and Aldehyde-Functionalized Multi-Arm PEG The following Example demonstrates that a hydrogel formed by reaction of an aldehyde-functionalized multi-arm PEG with an aminated carboxymethyldextran persists for prolonged periods of time in vitro.

Aqueous solutions containing P8-10-1-CHO (20 wt %) and CMDX-60-428 amine (20 wt %) were prepared in pure water. The pH of the CMDX-60-428 amine solution was adjusted to 9.48 by addition of 1 N NaOH. A gel test was run by adding 20 μL of each solution to a 3 mL test tube and stirring with a wooden rod. The gel formed in about 5 sec.

The hydrogel samples were prepared by mixing equal volumes of the two aqueous solutions described above using a double barrel syringe (Mixpac Systems AG (Rotkreuz, Switzerland) fitted with a 16 step static mixer (Mixpac Systems AG). After the hydrogels cured, the hydrogel samples were cut into 1.5 cm×0.68 cm strips. The strips were suspended in 20 mL vials with PBS buffer and placed inside a temperature-controlled shaker set at 80 rpm and 37° C. The samples were removed from the vials at various times, blotted to remove excess solution, and weighed. Then, the samples were returned to the vials. The results are given in Table 4. The results indicate that the hydrogel formed from P8-10-1-CHO (20 wt %) CMDX-60-428 amine (20 wt %) has a degradation time to 50% weight of about 500 hours.

TABLE 4

In Vitro Degradation of Hydrogel Formed from P8-10-1-CHO (20 wt %) and CMDX-60-428 Amine (20 wt %)

| Time (hours) | % Initial weight Sample 1 | % Initial weight Sample 2 |
|---|---|---|
| 0 | 100 | 100 |
| 1 | 289.5 | 273.8 |
| 2 | 320.9 | 308.8 |
| 4 | 331 | 310.1 |
| 6 | 343.1 | 315.8 |
| 7 | 344.4 | 305.7 |
| 23 | 346 | 303.2 |
| 31 | 325.5 | 288.6 |
| 47 | 281.2 | 251.1 |
| 54 | 238.1 | 232.8 |
| 119 | 214.6 | 205.7 |
| 150 | 194.1 | 169.7 |
| 191 | 213.8 | 199.4 |
| 221 | 191.6 | 179.2 |
| 287 | 137.7 | 151.4 |
| 335 | 98.3 | 135.6 |
| 386 | 56.9 | 84.2 |
| 479 | 51.5 | 66.6 |

Example 13

In Vitro Testing of Dextran Amine for Inhibition of *E. coli* Growth

The following Example demonstrates the antimicrobial activity of dextran amine by testing inhibition of *E. coli* growth.

A suspension culture of *E. coli* (strain K12, ATCC No. 25257) from American Type Culture Collection (ATCC; Manassas, Va.) was prepared by seeding an individual colony into 4 mL of Luria Broth (obtained from ATCC). The culture was incubated in a shaker overnight at 37° C. to allow the culture to reach the saturation point of cell growth. The concentration of *E. coli* in the saturated overnight culture was approximately $1 \times 10^9$ cells/mL. The saturated overnight culture (10 μL) was then seeded into 4 mL of Luria Broth, and the desired amount of a dextran amine was added, as indicated in Table 5. The culture was incubated in a shaker overnight at 37° C. Following the incubation, bacterial growth was quantified by measuring the optical density of the culture at 600 nm using a spectrophotometer. This method for determining in vitro antimicrobial activity has been shown to correlate with in vivo antimicrobial activity (Lee S H et al., *Journal of Pharmacy and Pharmacology* April 2003; 55:559-66). The results are summarized in Table 5. The bacteriostatically effective amount of dextran amine, i.e., the amount of the dextran amine that produced a 0.5 log decrease in bacterial growth, is also given in the Table. The bacteriostatically effective amount of the dextran amine was estimated from a plot of the log of bacterial growth (cells/mL) versus the volume of dextran amine solution added to the culture medium.

TABLE 5

Inhibition of *E. coli* Growth by Dextran Amines

| Example | Dextran amine | Volume Added (μL) | Bacterial Growth (cells/mL) | Bacteriostatically Effective Amount (mg/mL) |
|---|---|---|---|---|
| 13 | D10-247 amine 10 wt % | 0 | $1.0 \times 10^9$ | ≥5 |
| | | 20 | $7.1 \times 10^8$ | |
| | | 50 | $1.7 \times 10^8$ | |

What is claimed is:

1. A kit comprising:
   a) at least one aminated polysaccharide containing primary amine groups, said at least one aminated polysaccharide having a weight-average molecular weight of about 1,000 to about 1,000,000 Daltons and an equivalent weight per primary amine group of about 100 to about 3400 Daltons, wherein the at least one aminated polysaccharide is aminated dextran or aminated carboxymethyldextran; and
   b) at least one water-dispersible, aldehyde-functionalized multi-arm polyether having at least three arms wherein at least three of the arms are terminated with an aldehyde group, wherein said water-dispersible, aldehyde-functionalized multi-arm polyether has a number-average molecular weight of about 450 to about 200,000 Daltons.

2. The kit according to claim 1, wherein the aminated polysaccharide is a component of a first aqueous solution or dispersion and the water-dispersible, aldehyde-functionalized multi-arm polyether is a component of a second aqueous solution or dispersion.

3. The kit according to claim 1, wherein the aminated polysaccharide and the water-dispersible, aldehyde-functionalized multi-arm polyether are finely divided powders.

4. The kit according to claim 1, wherein the water-dispersible, aldehyde-functionalized multi-arm polyether is selected from the group consisting of aldehyde-terminated star polyethylene oxides, aldehyde-terminated dendritic polyethylene oxides, aldehyde-terminated comb polyethylene oxides, aldehyde-terminated star polypropylene oxides, aldehyde-terminated dendritic polypropylene oxides, aldehyde-terminated comb polypropylene oxides, aldehyde-terminated star polyethylene oxide-polypropylene oxide copolymers, aldehyde-terminated dendritic polyethylene oxide-polypropylene oxide copolymers, and aldehyde-terminated comb polyethylene oxide-polypropylene oxide copolymers.

5. The kit according to claim 4, wherein the water-dispersible, aldehyde-functionalized multi-arm polyether is a four-arm PEG tetra(thiomethylaldehyde), an eight-arm PEG octa(thiomethylaldehyde), or an eight-arm PEG octa-aldehyde.

6. The kit according to claim 1, wherein the aminated polysaccharide is aminated dextran and the water-dispersible, aldehyde-functionalized multi-arm polyether is a four-arm PEG tetra(thiomethylaldehyde), an eight-arm PEG octa(thiomethylaldehyde), or an eight-arm PEG octa-aldehyde.

7. The kit according to claim 1, wherein the aminated polysaccharide is aminated carboxymethyldextran and the water-dispersible, aldehyde-functionalized multi-arm polyether is an eight-arm PEG octa-aldehyde.

8. A dried hydrogel product formed by a process comprising the steps of:
  a) combining (i) a first solution or dispersion comprising at least one aminated polysaccharide containing primary amine groups in a first solvent, said aminated polysaccharide having a weight-average molecular weight of about 1,000 to about 1,000,000 Daltons and an equivalent weight per primary amine group of about 100 to about 3400 Daltons, wherein the at least one aminated polysaccharide is aminated dextran or aminated carboxymethyldextran; with (ii) a second solution or dispersion comprising at least one water-dispersible, aldehyde-functionalized multi-arm polyether having at least three arms in a second solvent, wherein at least three of the arms of said multi-arm polyether are terminated by an aldehyde group, said water-dispersible, aldehyde-functionalized multi-arm polyether having a number-average molecular weight of about 450 to about 200,000 Daltons, to form a hydrogel, wherein the first solvent is either the same as or different from the second solvent; and
  b) treating the hydrogel to remove at least a portion of said first solvent and said second solvent to form the dried hydrogel.

9. The dried hydrogel according to claim 8, wherein said dried hydrogel is in the form of a film.

10. The dried hydrogel according to claim 8, wherein the process further comprises comminuting the dried hydrogel to form finely divided particles.

11. A method for coating an anatomical site on tissue of a living organism comprising:
  a) applying to the anatomical site at least one aminated polysaccharide containing primary amine groups, said at least one aminated polysaccharide having a weight-average molecular weight of about 1,000 to about 1,000,000 Daltons and an equivalent weight per primary amine group of about 100 to about 3400 Daltons, wherein the at least one aminated polysaccharide is aminated dextran or aminated carboxymethyldextran; followed by
  b) applying to the anatomical site at least one water-dispersible, aldehyde-functionalized multi-arm polyether having at least three arms wherein at least three of the arms are terminated with an aldehyde group, wherein said water-dispersible, aldehyde-functionalized multi-arm polyether has a number-average molecular weight of about 450 to about 200,000 Daltons; or
  c) applying to the anatomical site the polyether of step b) followed by applying to the anatomical site the aminated polysaccharide of step a) and mixing the polyether and the aminated polysaccharide on the anatomical site; or
  d) premixing the aminated polysaccharide of step a) and the polyether of step b) to form a mixture and applying the mixture to the anatomical site.

12. The method according to claim 11, wherein the aminated polysaccharide is a component of a first aqueous solution or dispersion and the water-dispersible, aldehyde-functionalized multi-arm polyether is a component of a second aqueous solution or dispersion.

13. The method according to claim 12, wherein the aminated polysaccharide and the water-dispersible, aldehyde-functionalized multi-arm polyether are finely divided powders.

14. A composition comprising the reaction product of:
  a) at least one aminated polysaccharide containing primary amine groups, said at least one aminated polysaccharide having a weight-average molecular weight of about 1,000 to about 1,000,000 Daltons and an equivalent weight per primary amine group of about 100 to about 3400 Daltons, wherein the at least one aminated polysaccharide is aminated dextran or aminated carboxymethyldextran; and
  b) at least one water-dispersible, aldehyde-functionalized multi-arm polyether having at least three arms wherein at least three of the arms are terminated with an aldehyde group, wherein said water-dispersible, aldehyde-functionalized multi-arm polyether has a number-average molecular weight of about 450 to about 200,000 Daltons.

15. The composition according to claim 14, wherein the water-dispersible, aldehyde-functionalized multi-arm polyether is selected from the group consisting of aldehyde-terminated star polyethylene oxides, aldehyde-terminated dendritic polyethylene oxides, aldehyde-terminated comb polyethylene oxides, aldehyde-terminated star polypropylene oxides, aldehyde-terminated dendritic polypropylene oxides, aldehyde-terminated comb polypropylene oxides, aldehyde-terminated star polyethylene oxide-polypropylene oxide copolymers, aldehyde-terminated dendritic polyethylene oxide-polypropylene oxide copolymers, and aldehyde-terminated comb polyethylene oxide-polypropylene oxide copolymers.

16. The composition according to claim 15, wherein the water-dispersible, aldehyde-functionalized multi-arm polyether is a four-arm PEG tetra(thiomethylaldehyde), an eight-arm PEG octa(thiomethylaldehyde), or an eight-arm PEG octa-aldehyde.

* * * * *